United States Patent
Ambro

(10) Patent No.: US 11,179,161 B1
(45) Date of Patent: Nov. 23, 2021

(54) LIGATION CLIPS WITH ANTI-MIGRATION FEATURES

(71) Applicant: A2 Medical Systems LLC, Richland, MI (US)

(72) Inventor: Andrew J. Ambro, Richland, MI (US)

(73) Assignee: A2 Medical Systems LLC, Richland, MI (US)

(*) Notice: Subject to any disclaimer, the term of this patent is extended or adjusted under 35 U.S.C. 154(b) by 0 days.

(21) Appl. No.: 17/343,517

(22) Filed: Jun. 9, 2021

Related U.S. Application Data

(63) Continuation of application No. PCT/US2020/041119, filed on Jul. 8, 2020.

(51) Int. Cl.
*A61B 17/122* (2006.01)
*A61B 17/128* (2006.01)

(52) U.S. Cl.
CPC .......... *A61B 17/122* (2013.01); *A61B 17/128* (2013.01)

(58) Field of Classification Search
CPC ................ A61B 17/122; A61B 17/128; A61B 17/01222; A61B 17/0487; A61B 17/08; A61B 17/083; A61B 17/12
See application file for complete search history.

(56) References Cited

U.S. PATENT DOCUMENTS

| | | | |
|---|---|---|---|
| 4,834,096 A | 5/1989 | Oh | |
| 6,863,675 B2 | 3/2005 | Wilson | |
| 9,220,507 B1 * | 12/2015 | Patel | A61B 17/064 |
| D808,522 S | 1/2018 | Cannady | |
| 10,265,079 B2 | 4/2019 | Brodaczewski | |
| 10,335,157 B2 | 7/2019 | Patel | |
| 2005/0165421 A1 | 7/2005 | Wilson | |
| 2008/0312670 A1 | 12/2008 | Lutze | |
| 2014/0058411 A1 * | 2/2014 | Soutorine | A61B 17/1285 606/142 |
| 2017/0209149 A1 | 7/2017 | Menn | |
| 2017/0311954 A1 * | 11/2017 | Brodaczewski | A61B 17/122 |

(Continued)

FOREIGN PATENT DOCUMENTS

KR 101377429 B1 3/2014

OTHER PUBLICATIONS

Park, Hye Lyun, PCT International Search Report for International Application No. PCT/US2020/041119, dated Apr. 8, 2021, 4 pages, Korean Intellectual Property Office, Daejeon, Republic of Korea.

(Continued)

*Primary Examiner* — Brooke Nicole Labranche
(74) *Attorney, Agent, or Firm* — Kevin E Flynn; Flynn IP Law

(57) ABSTRACT

A ligation clip with a hinge connecting a first leg to a second leg; a hook to allow the first leg and the second leg from the ligation clip in the first open position to become engaged to hold the ligation clip in a closed position with an inner side of the first leg facing the inner side of the second leg. The ligation clip having at least one tissue trap near the inner side of the first leg. The tissue trap having at least one tissue plow. The ligation clip in an initial position after closure upon a vessel resists movement along the vessel as the at least one tissue plow drives tissue into the at least one tissue trap so that trapped tissue resists further movement of the ligation clip away from the initial position after closure of the ligation clip.

13 Claims, 19 Drawing Sheets

(56) References Cited

U.S. PATENT DOCUMENTS

2018/0368852 A1* 12/2018 Foshee ............... A61B 17/0487
2019/0314031 A1   10/2019 Thomas
2020/0405317 A1* 12/2020 Wallace ............. A61B 17/1227

OTHER PUBLICATIONS

Park, Hye Lyun, PCT Written Opinion of the International Searching Authority for International Application No. PCT/US2020/041119, dated Apr. 8, 2021, 4 pages, Korean Intellectual Property Office, Daejeon, Republic of Korea.

Dekel, Yoram et al., Letters to the Editor—Hem-o-lok Clip Dislodgment Causing Death of the Donor After Laparoscopic Living Donor Nephrectomy, Transplantation, Sep. 27, 2008, vol. 86, Issue 6, p. 887 https://journals.lww.com/transplantjournal/Fulltext/2008/09270/ Hem_o_lok_Clip_Dislodgment_Causing_Death_of_the.22.aspx, doi: 10.1097/TP.0b013e31818620b1.

* cited by examiner

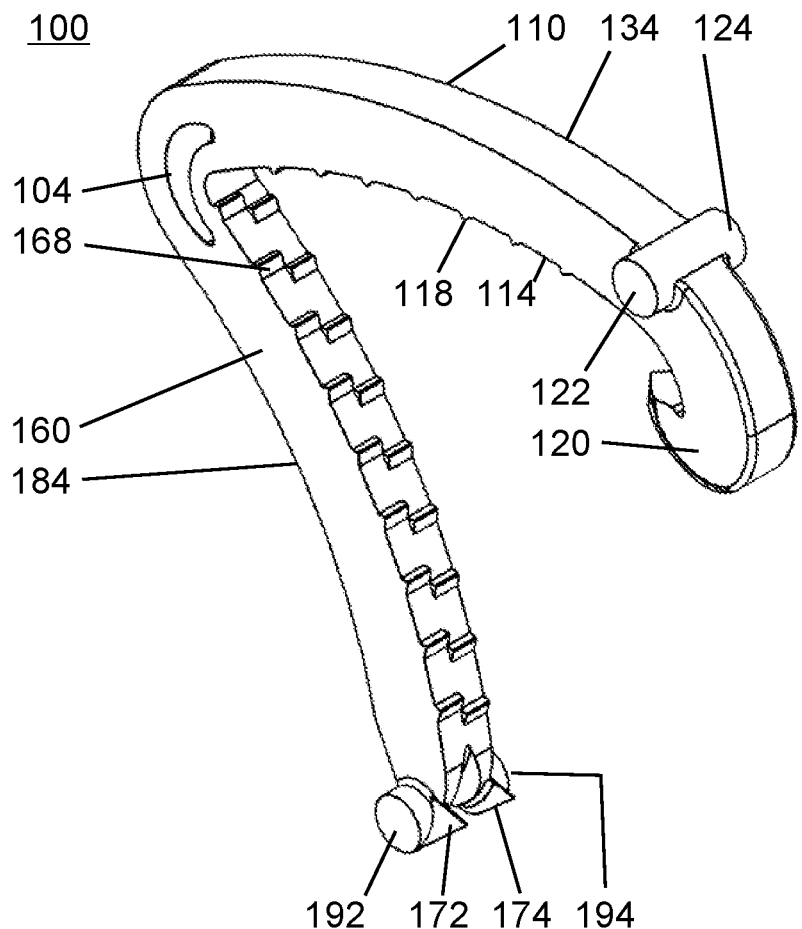
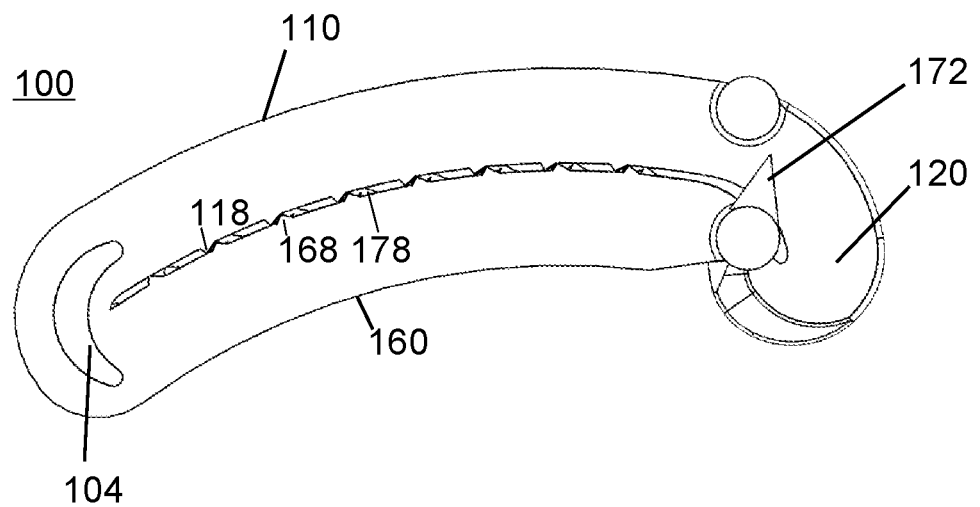

100

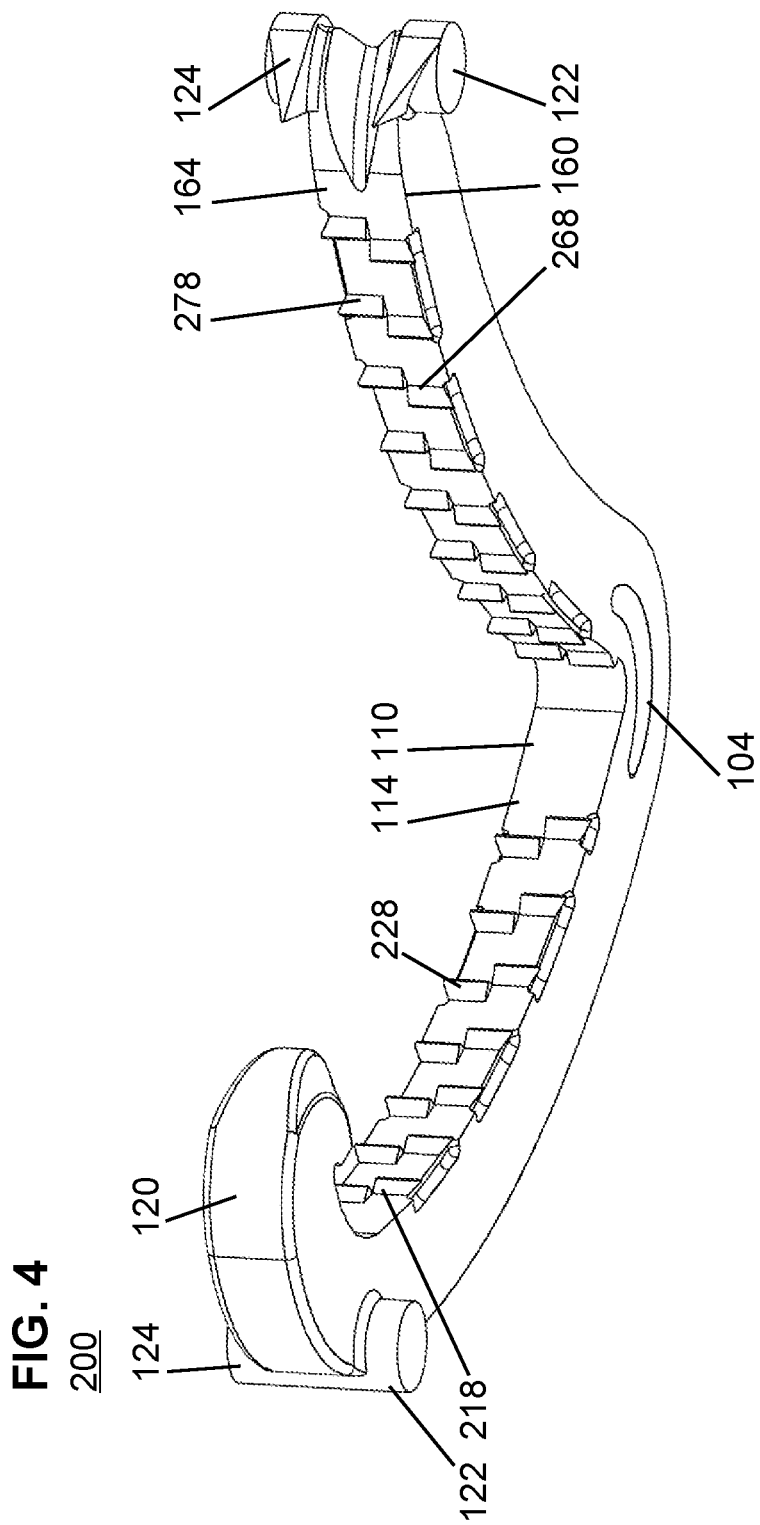

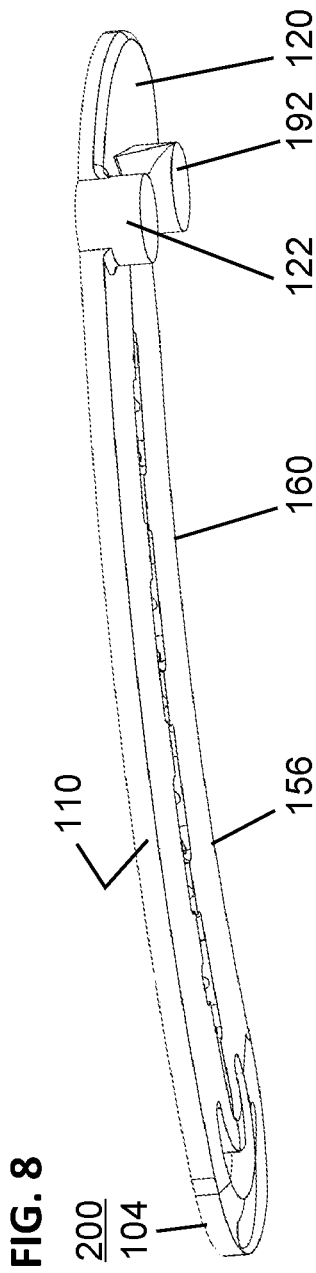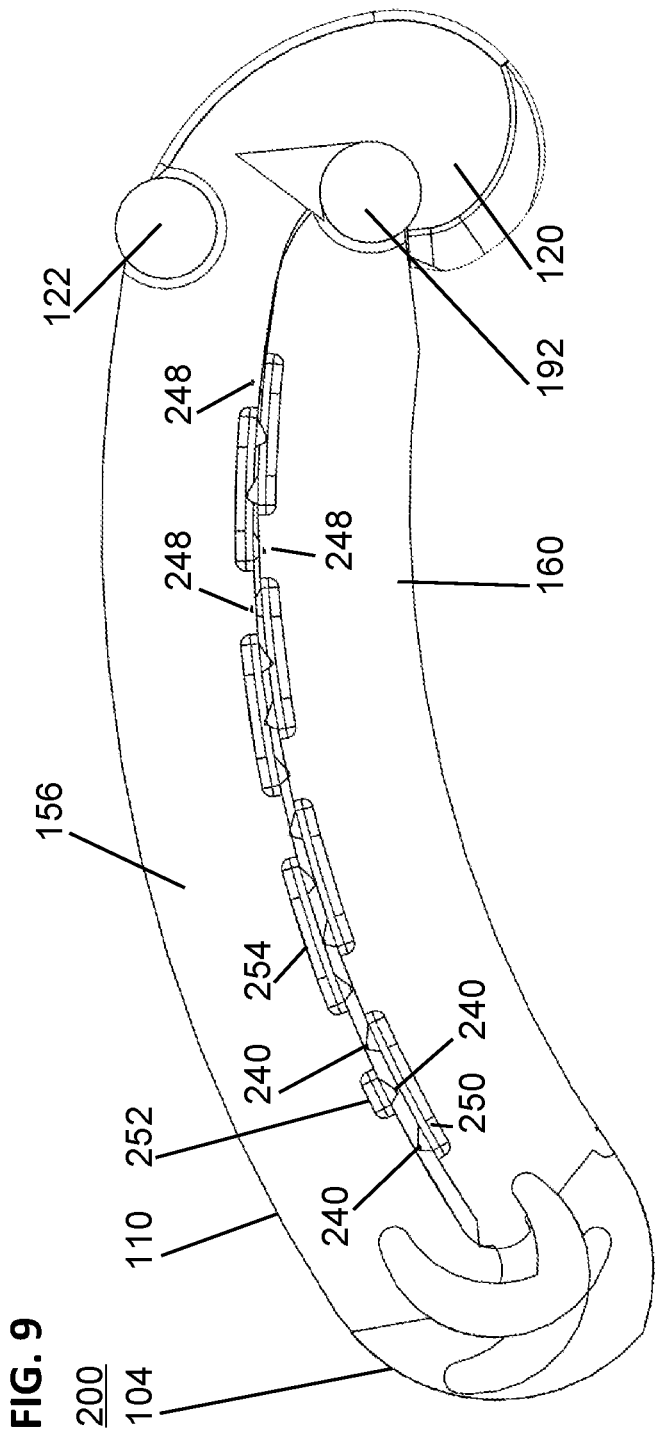

400

400

400

400

400

400

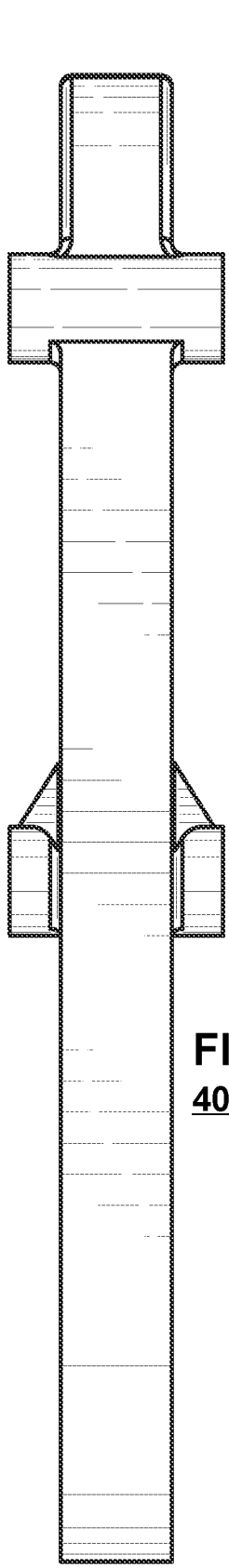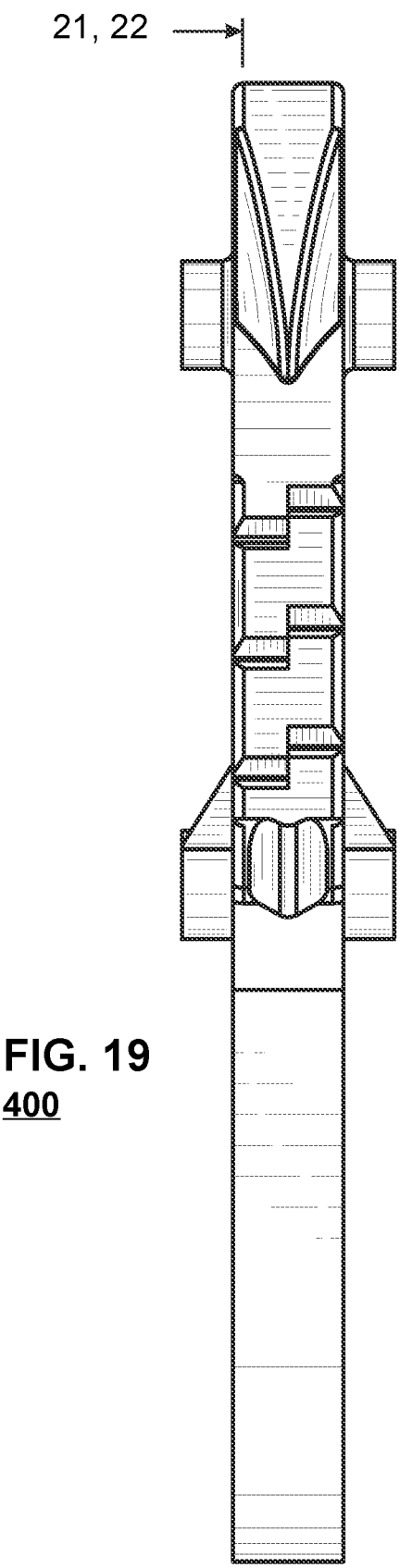
FIG. 18
400
FIG. 19
400

400

400

400

500

LIGATION CLIPS WITH ANTI-MIGRATION FEATURES

This application claims priority to co-pending and commonly assigned PCT application with International Application No. PCT/US2020/04119 filed Jul. 8, 2020 with title Ligation Clips with Anti-Migration Features. The '119 application is incorporated by reference herein.

BACKGROUND

Field of the Disclosure

This disclosure relates generally to ligating clips used to ligate or clamp a range of tissue materials during surgical procedures more particularly to polymer asymmetric surgical clips that have clip ends that latch to hold the clip in a closed position. Ligating clips are an alternative to suturing the tissue and are particularly useful in minimally invasive surgical procedures such as endoscopic surgical procedures.

Related Art

U.S. Pat. No. 4,834,096 for Plastic Ligating Clips which was issued more than thirty years ago is an example of polymer asymmetric surgical clip. Two curved legs connected by a hinge can be put into a closed position when a hook on a distal end of one leg latches with the distal end of the other leg. When closed, the surgical clip clamps a blood vessel between two substantially parallel faces of the pair of curved legs. Thus, the surgical clip is often called a ligating clip.

Subsequent developments in ligating clips have added teeth to the two substantially parallel faces of the curved legs to reduce any likelihood for movement of the ligating clip laterally with respect to the ligated vessel so that the ligating clip moves beyond the end of the ligated vessel and ceases ligation. These teeth need to provide grip without being traumatic as some uses of ligating clips call for removal and reuse of the temporarily blocked vessel. U.S. Design Pat. D808522 for Latching Ends of a Polymer Ligating Clip shows a modern ligating clip.

Ligating clips have to avoid traumatic injury of blood vessels as the use of the ligating clip is sometimes temporary. But ligating clips need staying power to avoid migration from the placed position on the blood vessel or other vessel when used permanently. An ongoing failure mode for polymer ligating clips is dislodgement—the movement ("migration") of the closed ligating clip to cease the desired ligation. Dislodgement leading to unsupervised flow through the non-occluded vessel may be fatal. See for example:

Hem-o-lok Clip Dislodgement Causing Death of the Donor After Laparoscopic Living Donor Nephrectomy—Letter to the Editor by Yoram Dekel et al. Transplantation: Sep. 27, 2008—Volume 86—Issue 6—p 887 (https removed)://journals.lww.com/transplantjournal/Fulltext/2008/09270/Control_of_the_Renal_Artery_and_Vein_with_the.22.aspx);

Barabino M, Luigiano C, Piccolo G, et al. Hem-o-lok clip migration into the duodenum after laparoscopic digestive surgery: a systematic review. Minerva Chir. 2019; 74(6): 496-500. doi:10.23736/S0026-4733.19.08152-5 (https removed)://pubmed.ncbi.nlm.nih.gov/31958943/;

Cormio, L., Massenio, P., Lucarelli, G. et al. Hem-o-lok clip: a neglected cause of severe bladder neck contracture and consequent urinary incontinence after robot-assisted laparoscopic radical prostatectomy. BMC Urol 14, 21 (2014).—://doi.org/10.1186/1471-2490-14-21 (Https removed)://bmcurol.biomedcentral.com/articles/10.1186/1471-2490-14-21#citeas;

Bientinesi, Riccardo & Di Gianfrancesco, Luca & Pugliese, Dario & D'Agostino, Daniele & Racioppi, Marco & Bassi, Poonam & Sacco, Emilio. (2014). Endourethral migration of a Hem-o-Lok Clip after robot-assisted laparoscopic radical prostatectomy. Urologia. 10.5301/uro.5000106, (https removed)//www.researchgate.net/publication/270908640_Endourethral_migration_of_a_Hem-o-Lok_Clip_after_robot-assisted_laparoscopic_radical_prostatectomy/citation/download.

Thus, improving a ligating clip to retain the ability to atraumatically ligate for temporary use but reduce the risk of dislodgement after closing of the surgical site is a long-desired solution to a critical need in ligating clips.

Vocabulary

Units.

Note that in order to provide focus on specific functions, the description below will reference various "units". In this context, a unit implies the required resources to perform a given set of functions. This may include a combination of electro-mechanical devices such as a microphone or a camera and the processing power to control the devices then manipulate the data obtained by the devices. In some instances, the functionality from several individually discussed units may be performed using physical components that are shared by several of the units discussed below. Unless explicit to the contrary, the word "or" should be interpreted as an inclusive or rather than an exclusive or. Thus, the default meaning of or should be the same as the more awkward and/or.

Or.

Unless explicit to the contrary, the word "or" should be interpreted as an inclusive or rather than an exclusive or. Thus, the default meaning of or should be the same as the more awkward and/or.

Proximal and Distal.

Proximal and distal should be considered relative to the hinge of the ligating clip.

Set.

Unless explicit to the contrary, the word "set" should be interpreted as a group of one or more items.

Gne and Gnes.

To avoid the awkward uses of he/she and his/her or the potentially confusing singular use of they and their, this application uses the gender-neutral pronoun gne and the possessive gnes. ExampleGne parked gnes car in the parking lot.

Substantially.

Frequently, when describing an industrial process, it is useful to note that a given parameter is substantially met. Examples may be substantially parallel, substantially perpendicular, substantially uniform, and substantially flat. In this context, substantially X means that for purposes of this industrial process it is X. So, something that may not be absolutely parallel but is for all practical purposes parallel, is substantially parallel. Likewise, mixed air that has substantially uniform temperature would have temperature deviations that were inconsequential for that industrial process.

As recognized in C. E. Equipment Co. v. United States, 13 U.S.P.Q.2d 1363, 1368 (Cl. Ct. 1989), the word "substantially" in patent claims gives rise to some definitional leeway—thus the word "substantially" may prevent avoidance of infringement by minor changes that do not affect the results sought to be accomplished.

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provides below as one of skill in the art will recognize that inventive concepts illustrated in various examples can be combined together in order to address a specific application.

One way to summarize some of the teachings of the present disclosure is that anti-migration features called tissue plows and tissue traps are included in ligation clips to prevent the closed ligating clips from slipping axially along the distal ends of ligated vessels after application. This type of slipping or migration may result in the ligating clip falling off the vessel resulting in loss of ligation and subsequent hemorrhaging.

The tissue traps are sub-flush to flush relative to the side faces of the ligating clip legs so the overall size of the ligating clip is not increased. Those of skill in the art may express this concept as the original geometry of the clip is not altered.

The tissue plows have negative angles (inward) against outside flat side faces of the clip legs. These tissue plows engage with vessel tissue as the clip legs are closed to help displace compressed tissue in and around the sub-flush tissue traps and keep tissue secure with the tissue traps once the ligating clip has locked closed. The tissue plows and tissue traps also work together in a cupping action to reduce clip migration risks. This reduces risk of clip slippage/migration by effectively axially engaging tissue on the ligated vessel.

Some aspects of the teachings of the present disclosure may be expressed as a ligation clip with a hinge connecting a first leg to a second leg; a hook to allow the first leg and the second leg from the ligation clip in the first open position to become engaged to hold the ligation clip in a closed position with an inner side of the first leg facing the inner side of the second leg. The ligation clip having first side between the hinge and the hook and a second side, opposite the first side, between the hinge and the hook. The first side of the first leg having at least one tissue trap near the inner side of the first leg. The tissue trap having at least one tissue plow extending from an edge of the tissue trap outward toward the inner side of the second leg and also away from the second side of the first leg. The ligation clip in an initial position after closure upon body tissue resists movement perpendicular to the first side as the at least one tissue plow drives tissue into the at least one tissue trap so that trapped tissue resists further movement of the ligation clip away from the initial position after closure of the ligation clip.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 1 is a top side, front side, left side perspective view of a ligation clip 100 without the anti-migration features and in the open position.

FIG. 3 shows a left side view of a new ligation clip shown in FIG. 1 again without the anti-migration features and in the closed position.

FIG. 4 shows a first embodiment of an improved ligation clip 200 with anti-migration features as seen from a similar perspective as used in FIG. 2.

FIG. 8 is a cross section of a closed ligation clip 200. The view is a perspective view of the top side and left side of the ligation clip 200.

FIG. 9 is the same cross section of closed ligation clip 200 shown in FIG. 8 but looking at the left elevation view.

FIG. 15 indicates the cross section that is used for FIG. 20.

FIG. 18 is a top plan view of ligation clip 400 without other element numbers obscuring the image.

FIG. 19 is a bottom plan view of ligation clip 400 without other element numbers obscuring the image.

DETAILED DESCRIPTION

Figure 2:
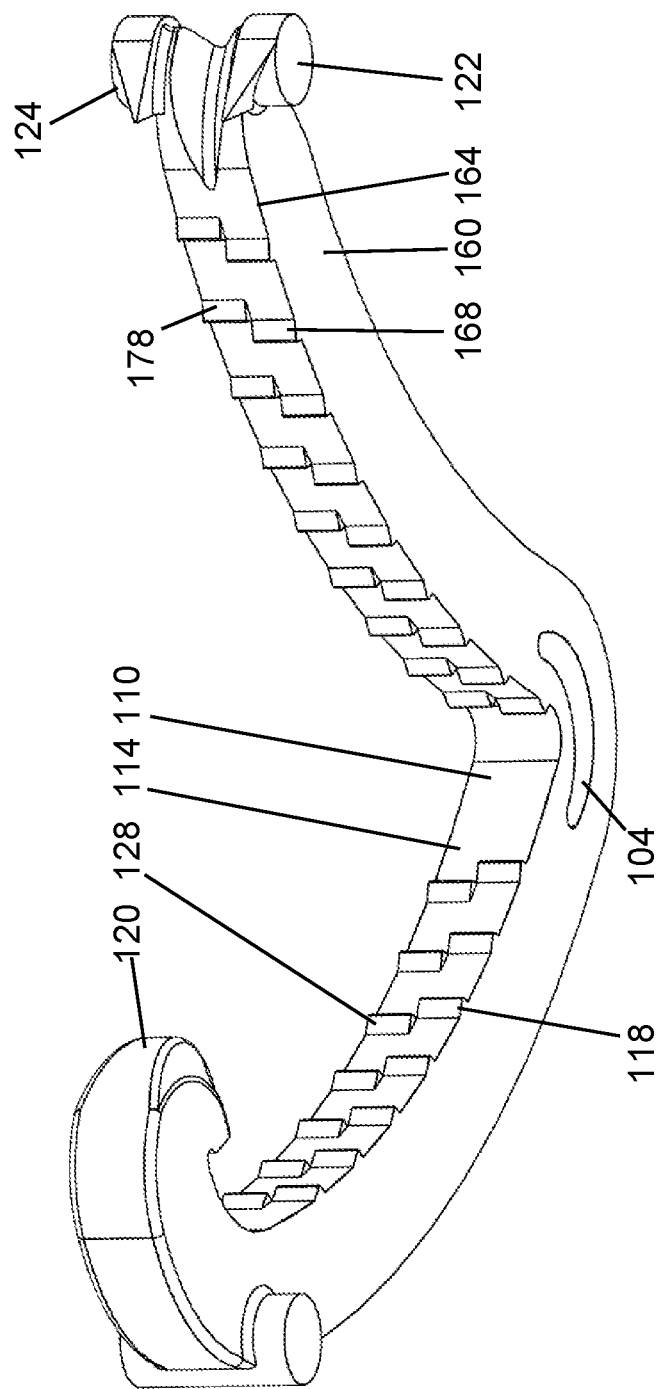
FIG. 2 shows the ligation clip from FIG. 1 from another perspective showing the left side of the ligation clip 100 with the hinge 104 down and the hook end 120 and tissue piercing points 172 and 174 up.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies.

FIG. 1 shows a new ligation clip without the anti-migration features so that more conventional components can be introduced. FIG. 1 is a top side, front side, left side perspective view of a ligation clip 100 in the open position. The ligation clip 100 has a hinge 104 between a concave leg 110 and a convex leg 160. The concave leg 110 has an inner concave surface 114 and an outer convex surface 134. The convex leg 160 has an inner convex surface 164 and an outer concave surface 184. The concave leg 110 has a hook end 120 which engages the convex leg 160 to lock the ligation clip 100 in the closed position. The concave leg 110 has a pair of bosses 122 and 124 that may be used to position the concave leg 110 in a clip applier tool.

The convex leg 160 has a pair of tissue piercing points 172 and 174 that are helpful in preventing thin layers of tissue from obstructing the movement of the hook end 120 to engage the convex leg 160. The convex leg 160 has a pair of bosses: boss 192 and boss 194 that may be used to position the concave leg 110 in a clip applier tool.

Gripper Teeth.

The convex leg 160 has a left set of gripper teeth 168 and a staggered right set of gripper teeth 178. The concave leg 110 has a left set of gripper teeth 118 and a right set of gripper teeth 128 (not visible here). When the concave leg 110 is held in a closed locked position near the convex leg 160, the four sets of gripper teeth (168, 178, 118, and 128) gently hold the entrapped tissue but do so in an atraumatic way as the use of the ligation clip 100 may be temporary and long term damage to the entrapped tissue is not desirable.

FIG. 2 shows the ligation clip from FIG. 1 from another perspective showing the left side of the ligation clip 100 with the hinge 104 down and the hook end 120 and tissue piercing points 172 and 174 up. This view allows the left set of gripper teeth 118 and the right set of gripper teeth 128 to be seen on the inner concave surface 114 on concave leg 110. Likewise, the left set of gripper teeth 168 and the right set of gripper teeth 178 are visible on the inner convex surface 164 on convex leg 160.

FIG. 3 shows a left side view of a new ligation clip shown in FIG. 1 again without the anti-migration features. In FIG. 3 the ligation clip is in the closed position. In the closed position the left set of gripper teeth 118 from the concave leg 110 make contact with the left set of gripper teeth 268 of the convex leg 160 so that the model shows the ligation clip 100 at the point of contact. Likewise, the right side of gripper teeth 128 (not visible here) from the concave leg 110 make contact with the right-side gripper teeth 178 from the convex leg 160. However, in actual use, the teeth do not make uniform contact as there is tissue such as blood vessels between the concave leg 110 and the convex leg 160. The teeth, which are designed to provide an atraumatic non-piercing grip, are limited in their ability to preclude migration of the ligation clip to the end of the captured tissue. If the ligation clip 100 is pulled beyond the end of the captured tissue, then a blood vessel or other ligated conduit may reopen after the surgical site has been closed.

FIG. 4 shows a first embodiment of an improved ligation clip 200 with anti-migration features. FIG. 4 shows the ligation clip 200 from a similar perspective as used in FIG. 2. FIG. 4 shows the left side of the ligation clip 200 with the hinge 104 down and the hook end 120 and tissue piercing points 172 and 174 up. This view allows the left set of gripper teeth 218 and the right set of gripper teeth 228 to be seen on the inner concave surface 114 on concave leg 110. Likewise, the left set of gripper teeth 268 and the right set of gripper teeth 278 are visible on the inner convex surface 164 on convex leg 160. Boss 122 and boss 124 may be used by a clip applying device.

Tissue Plows and Tissue Traps.

Figure 5:
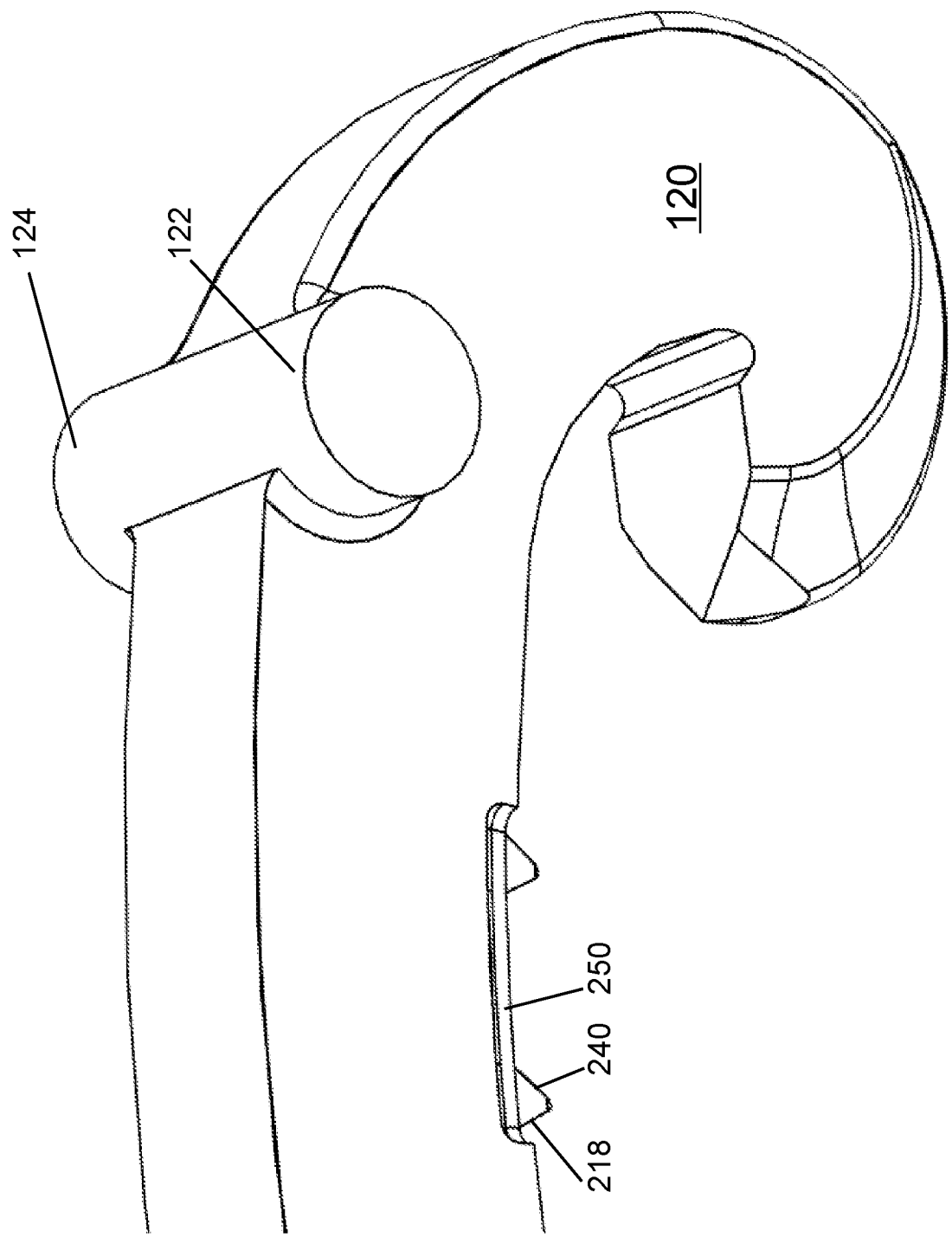
FIG. 5 shows only a portion of an open ligation clip 200 including the previously introduced hook end 120, boss 122, and boss 124.

FIG. 5 shows only a portion of an open ligation clip 200 including the previously introduced hook end 120, boss 122, and boss 124. FIG. 5 shows that the left set of gripper teeth 118 have been modified so that the lateral faces of the gripper teeth 218 are no longer flat as shown in connection with ligation clip 100. Instead the gripper teeth 218 have tissue plows 240 that guide tissue into tissue traps 250. When a closed ligation clip 200 moves laterally along the ligated tissue towards the end of the ligated tissue, the tissue plows 240 will guide tissue up into the tissue traps 250. The tissue trapped by the combination of the tissue plows 240 and the tissue traps 250 will resist continued lateral motion of the closed ligation clip 200 thus reducing the risk of a closed ligation clip migrating beyond the end of the occluded vessel to lead to a dislodgement of the ligation clip.

Figure 6:
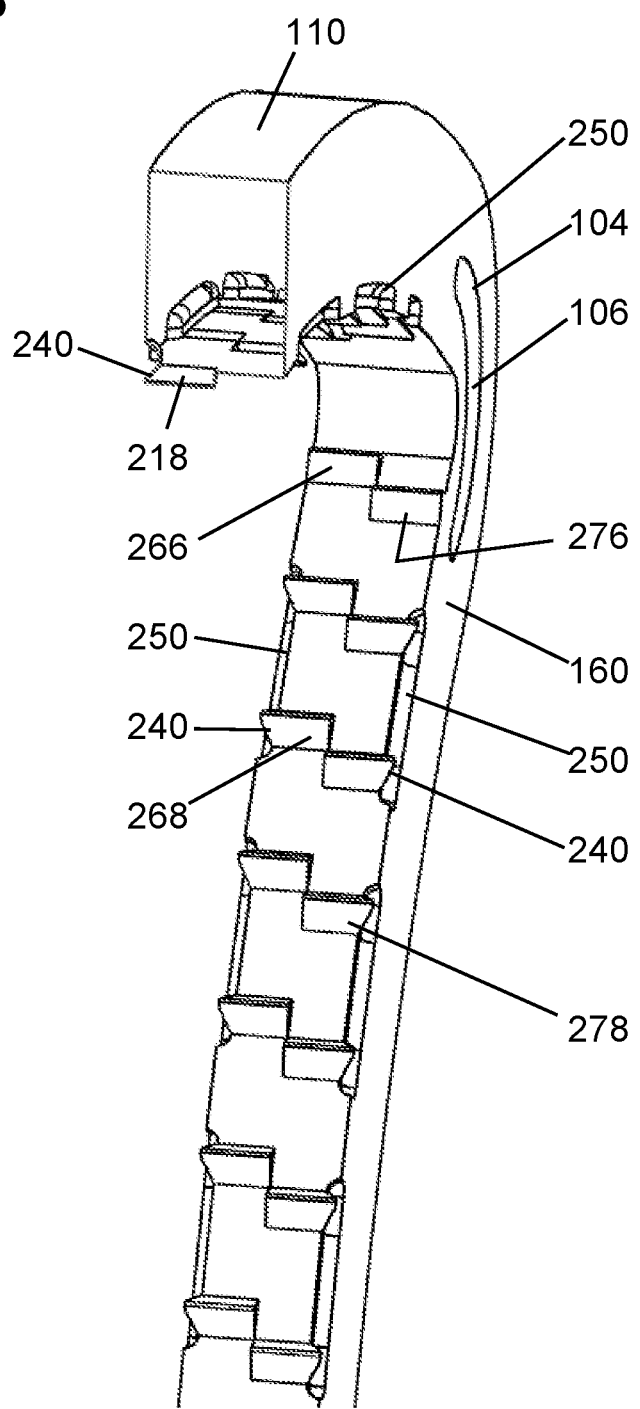
FIG. 6 shows the open ligation clip 200 at a cross section taken close to the hook end 120 of the concave leg 110.

FIG. 6 shows a cross section taken close to the hook end 120 of the concave leg 110. The cross section is taken through a tissue plow 240 on a gripper tooth from the left set of gripper teeth 268. FIG. 6 shows the right set of gripper teeth 228 on the concave leg 110 also have tissue plows 240 to direct tissue into tissue traps 250. The CAD rendering shows the ligation clip 200 as hollow so the cross section reveals the inner surface of the tissue traps 250 for the left side of the concave leg 110.

A portion of the convex leg 160 extending from the hinge 104 is visible and shows that both the left set of gripper teeth 268 and the right set of gripper teeth 278 on the convex leg 160 have tissue plows 240 to push tissue into tissue traps 250. Note that a left gripper tooth 266 above the hinge void 106 in the hinge 104 does not have a tissue plow 240 or an associated tissue trap 250. Likewise, a right gripper tooth 276 above the hinge void 106 in the hinge 104 does not have a tissue plow 240 or an associated tissue trap 250. The decision to have tissue plows 240 and tissue traps 250 for a full set of gripper teeth may be driven by factors such as a desire to simplify the mold near the hinge void 106 or just a decision not to have a smaller tissue trap 250 for a single gripper tooth when there are an odd number of gripper teeth and there is a use of a two tooth tissue trap 250 as shown in connection with ligation clip 200.

Figure 7:
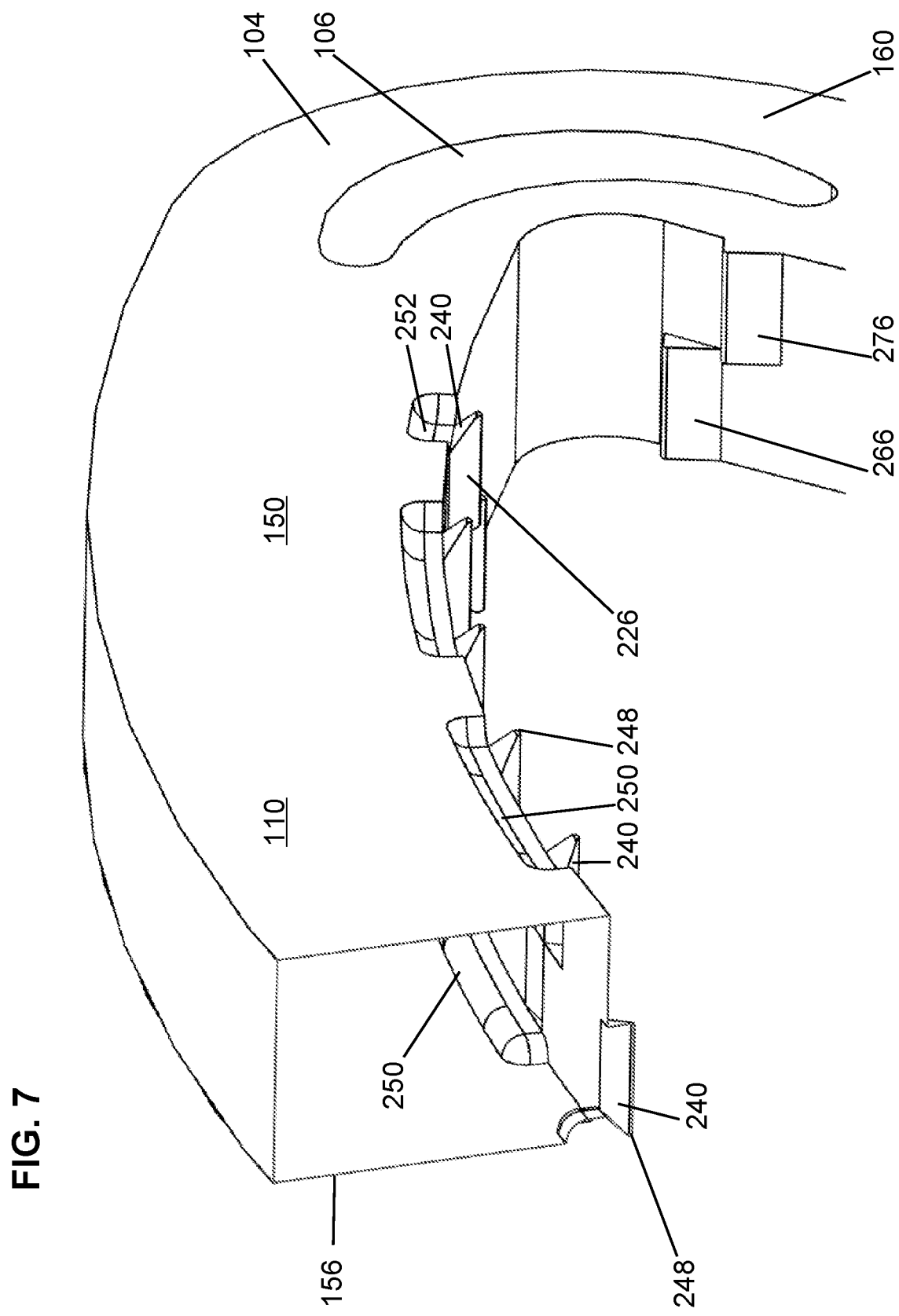
FIG. 7 shows the same cross section on ligation clip 200 but enlarged and at a slightly different angle.

FIG. 7 shows the same cross section on ligation clip 200 but enlarged and at a slightly different angle. Note that whereas gripper tooth 266 and gripper tooth 276 did not have a tissue plow 240 or tissue trap 250, gripper tooth 226 from the right set of gripper teeth 228 on the concave leg 110 does have a tissue plow 240 directing tissue into a single tooth tissue trap 252.

The tissue plows 240 have plow tips 248 that may be substantially aligned with the right side 150 of the ligation clip 200 and to the left side 156 of the ligation clip 200.

Note that while it was easier to explain tissue plows 240 and tissue traps 250 by introducing the tissue plows 240 first, the tissue plows 240 can be created as an extension of the space defined by the tissue traps 250. Thus, the tissue plows 240 may be a byproduct of the formation of the tissue traps 250 as the trough of material is removed from the lateral edge of the leg undercuts the gripper tooth creating the tissue plows 240. An advantage of this relationship between the plow tips 248 and the sides of the ligation clip 200 is that the existence of the tissue plows 240 and tissue traps 250 does not preclude use of legacy ligation clip appliers that do not have these enhanced anti-migration features.

FIG. 8 is a cross section of a closed ligation clip 200. The view is a perspective view of the top side and left side of the ligation clip 200. Visible are previously described components provided here for orientation:

left side 156 of ligation clip 200;
a left portion of hinge 104;
a left portion of concave leg 110;
a left portion of convex leg 160;
boss 122; and
boss 192.

FIG. 9 is the same cross section of closed ligation clip 200 shown in FIG. 8 but looking at the left elevation view. FIG. 9 highlights the aggregate resistance to lateral motion relative to the hook/hinge axis of the ligation clip 200. A series of tissue traps 250 including three double tooth tissue traps 254 and one single tooth tissue trap 252 exist on the left side 156 of the ligation clip 200. As the ligation clip moves laterally, the tissue plows 240 work to press tissue between the tissue plow 240 and the tissue traps 250 (including the special case single tooth tissue trap 252). These trapped tissue wedges work to stop migration and avoid dislodgement. As there may be different types of tissue near the ligation and the ligation clip 200 will likely have a larger gap near the ligated vessel, the ability of the tissue plows 240 and tissue traps 250 to trap tissue wedges may not be uniform along the length of the ligation clip 200. However, if some tissue plow 240/tissue trap 250 pairs are effective in capturing a tissue wedge that should be sufficient to stop migration.

Note—those of skill in the art will recognize that a CAD model for creating an accurate model of an open ligation clip 200 has limitations and some unnatural artifacts when altered to form a closed ligation clip for use in discussing the innovative features. Thus, a careful observer will note that plow tips 248 from tissue plows 240 near the hook end 120 of the closed ligation clip 200 are erroneously displayed as being within the opposing leg instead of on top of the opposing leg. Those of skill in the art will recognize that the depiction of tissue plows 240 near the hinge 104 are sufficient to describe the operation of tissue plows 240.

If an appropriate cross section was taken to remove off-side gripper teeth from the cross section, a right-side elevation view of this ligation clip 200 would also show seven tissue plows 240 on the concave leg 110 and eight tissue plows 240 on the convex leg 160. The concave leg 110 would have one tissue trap 250 that was a single tooth tissue trap 252 and three double tooth tissue traps 254.

Other Tissue Trap Widths.

Ligation clip 200 use tissue traps 250 that were sufficiently wide that most were double tooth tissue traps 254 spanning a pair of gripper teeth and having two associated tissue plows 240. Using tissue traps 250 that are mostly serviced by a pair of tissue plows 240 is not a requirement of the present disclosure.

Figure 10:
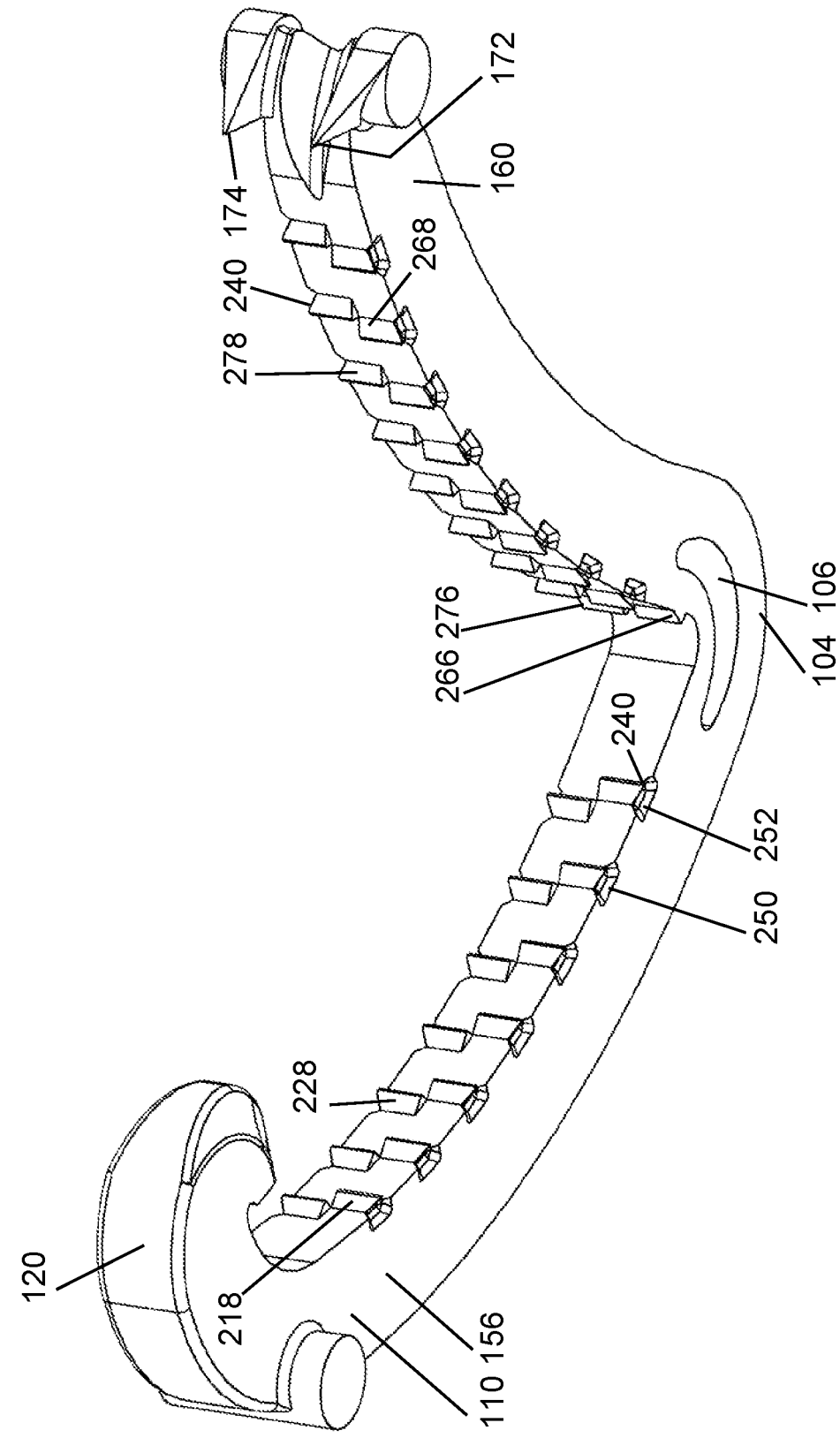
FIG. 10 shows a perspective view of the left side 156 of a ligation clip 300 with hook end 120 up and the tissue piercing points 172 and 174 up but with the hinge 104 down.

FIG. 10 shows a perspective view of the left side 156 of a ligation clip 300 with hook end 120 up and the tissue piercing points 172 and 174 up but with the hinge 104 down. All tissue traps 250 are single tooth tissue traps 252 with a single tissue plow 240. As with ligation clip 200, the gripper teeth 266 and 276 on the convex leg 160 above the hinge void 106 in the hinge 140 may be designed so that they do not have tissue traps 250 or tissue plows 240.

Figure 11:
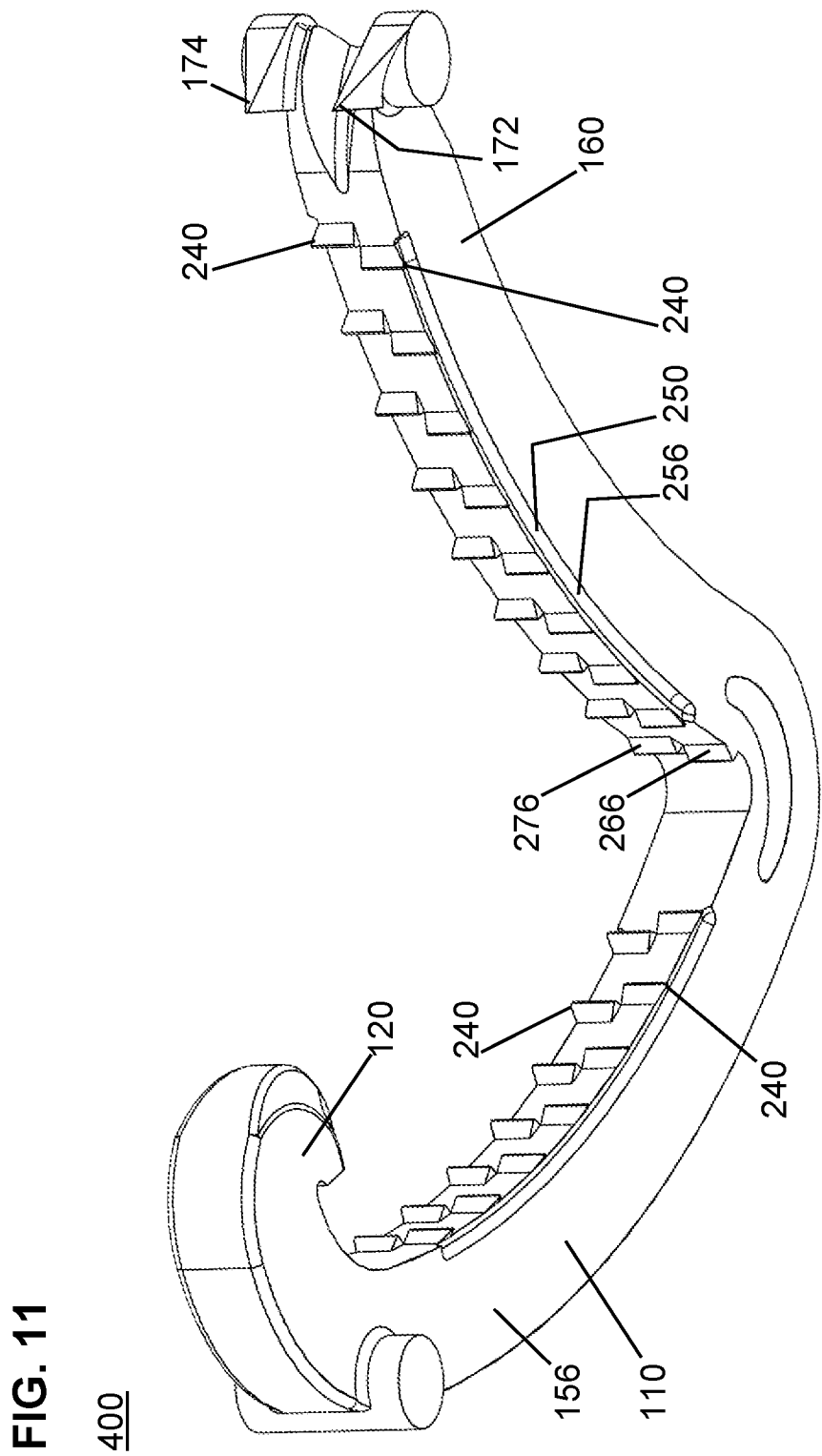
FIG. 11 shows a perspective view of the left side 156 of a ligation clip 400 with hook end 120 up and the tissue piercing points 172 and 174 up but with the hinge 104 down.

FIG. 11 shows a perspective view of the left side 156 of a ligation clip 400 with hook end 120 up and the tissue piercing points 172 and 174 up but with the hinge 104 down. All tissue traps 250 are merged tissue traps 256 with a single merged tissue trap 256 per side of the concave leg 110, and a single merged tissue trap 256 per side of the convex leg 160. Thus, each merged tissue trap 256 has a number of associated tissue plows 240. As with ligation clip 200 and ligation clip 300, the gripper teeth 266 and 276 on the convex leg 160 above the hinge void 106 in the hinge 140 may be designed so that they do not have and an associated tissue trap 250 or an associated tissue plow 240.

Figure 12:
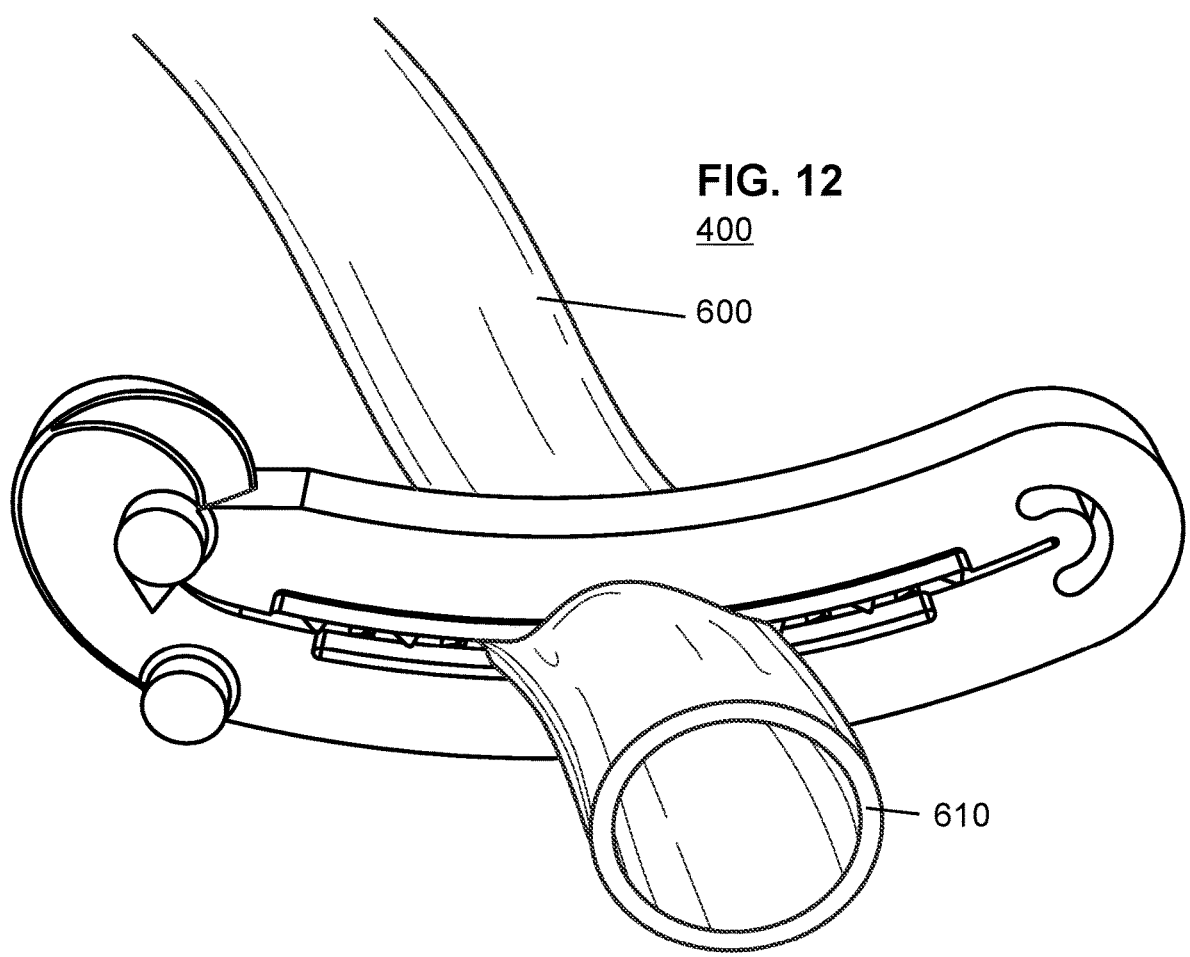
FIG. 12 shows the ligation clip 400 in a closed position and a ligated blood vessel.

FIG. 12 shows the ligation clip 400 in a closed position and a ligated blood vessel 600. In the closed position, the tissue plows will drive tissue up into the tissue traps to resist movement of the ligation clip 400 towards the open end 610 of the ligated vessel 600.

Figure 13:
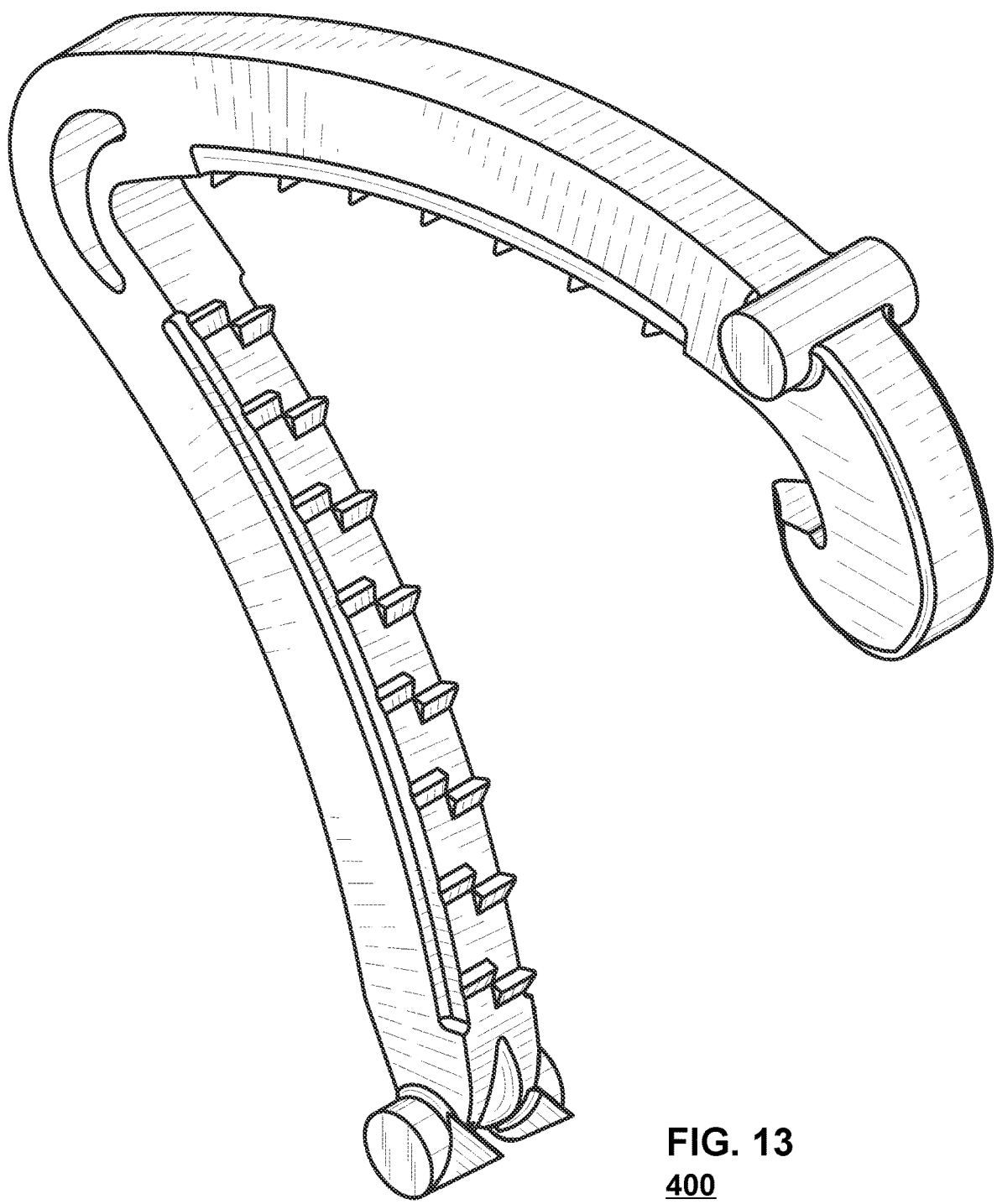
FIG. 13 is a top, front, left, perspective view of ligation clip 400 without other element numbers obscuring the image.

FIG. 13 is a top, front, left, perspective view of ligation clip 400 without other element numbers obscuring the image.

Figure 14:
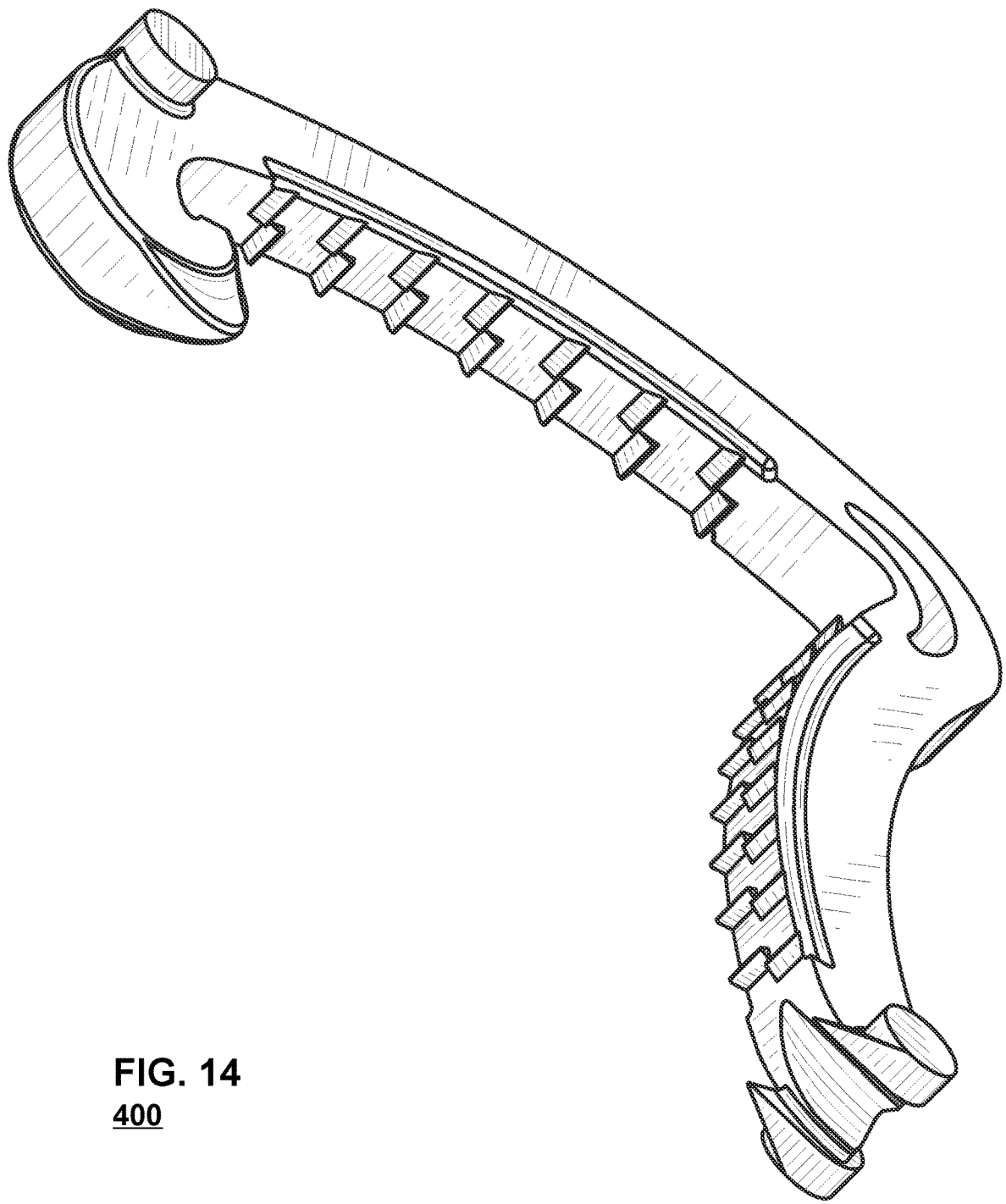
FIG. 14 is a front, right, perspective view of ligation clip 400 without other element numbers obscuring the image.

FIG. 14 is a front, right, perspective view of ligation clip 400 without other element numbers obscuring the image.

Figure 15:
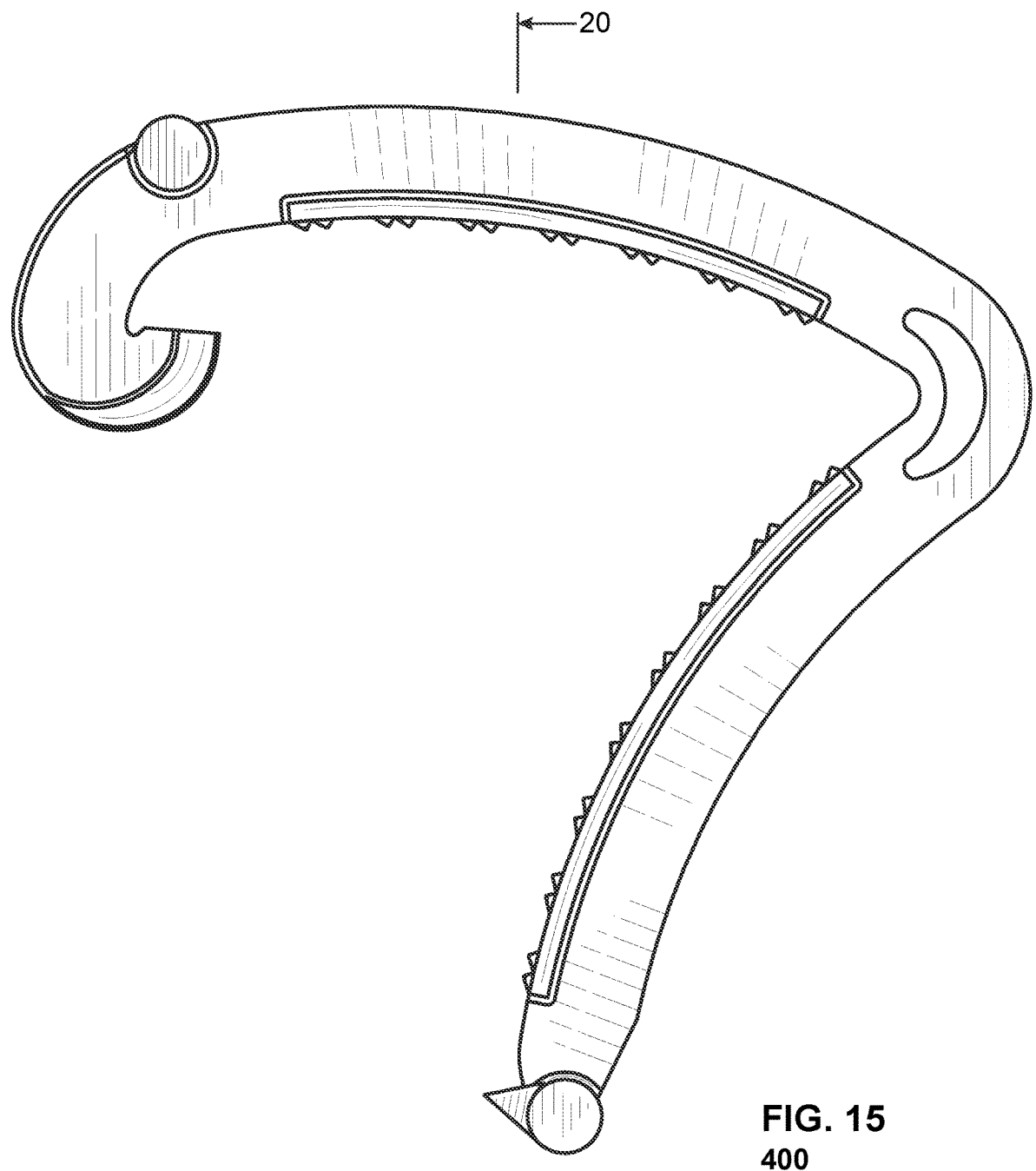
FIG. 15 is a right elevation view of ligation clip 400 without other element numbers obscuring the image.

FIG. 15 is a right elevation view of ligation clip 400 without other element numbers obscuring the image. FIG. 15 indicates the cross section that is used for FIG. 20.

Figure 16:
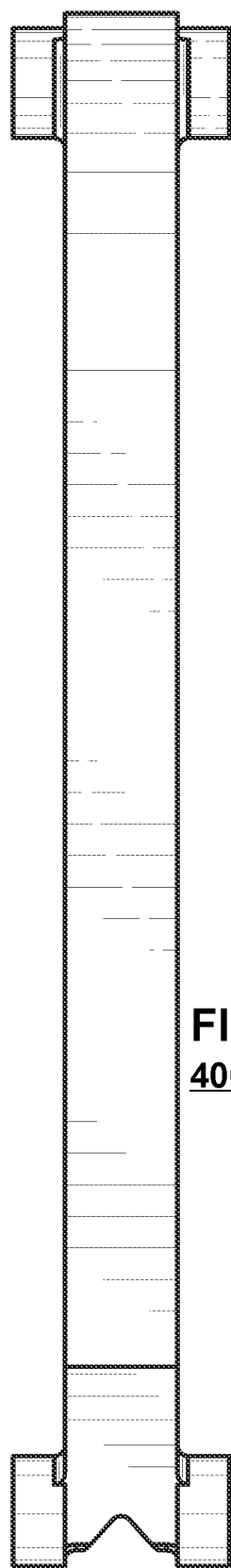
FIG. 16 is a front elevation view of ligation clip 400 without other element numbers obscuring the image.

FIG. 16 is a front elevation view of ligation clip 400 without other element numbers obscuring the image.

Figure 17:
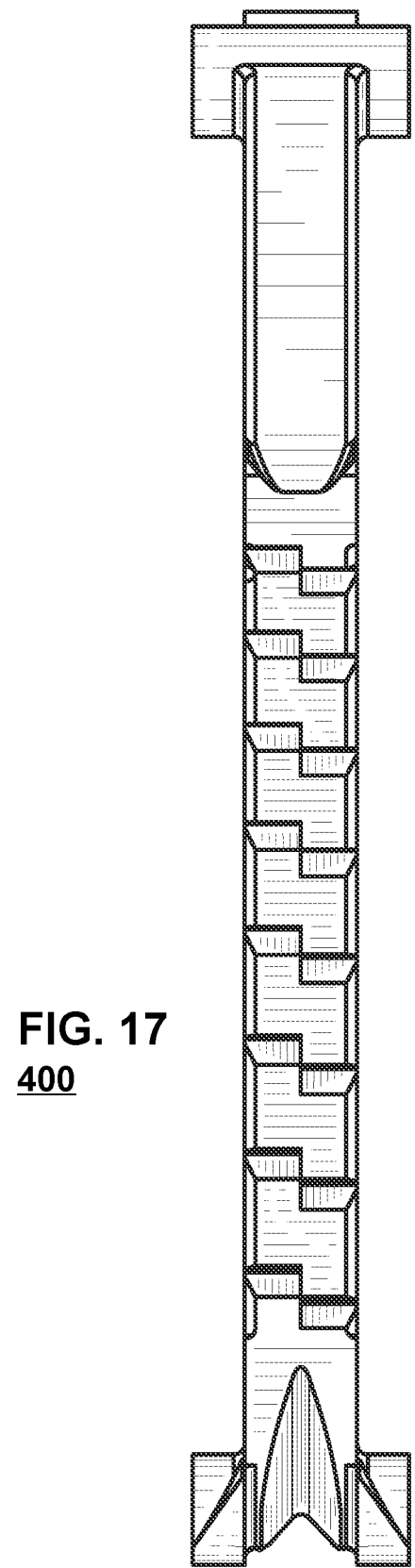
FIG. 17 is a rear elevation view of ligation clip 400 without other element numbers obscuring the image.

FIG. 17 is a rear elevation view of ligation clip 400 without other element numbers obscuring the image.

FIG. 18 is a top plan view of ligation clip 400 without other element numbers obscuring the image.

FIG. 19 is a bottom plan view of ligation clip 400 without other element numbers obscuring the image.

Figure 20:
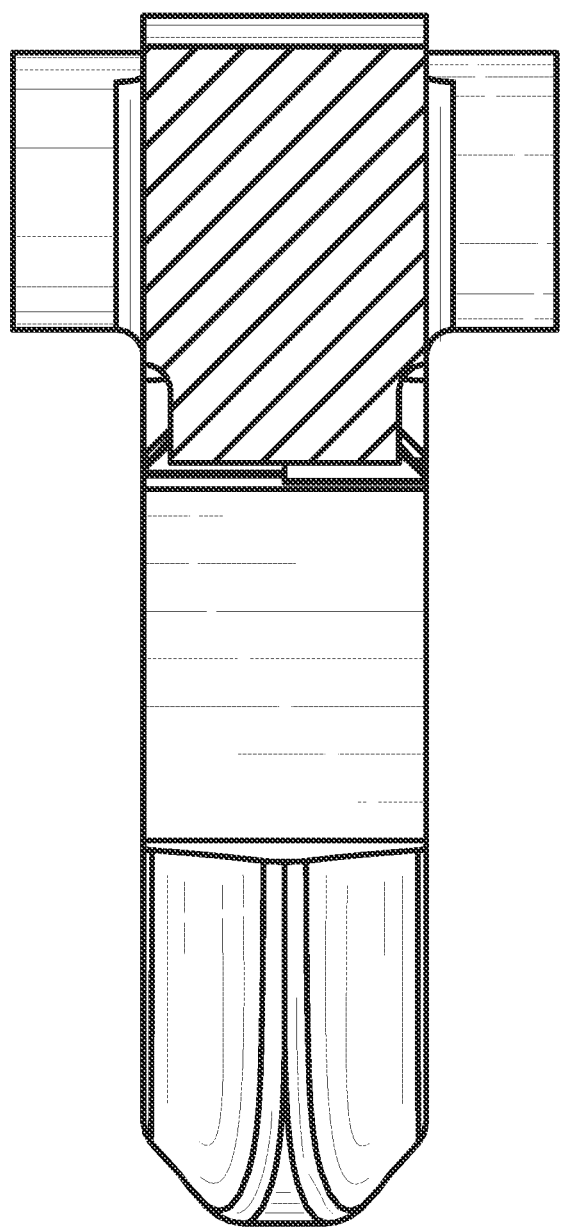
FIG. 20 is a cross section view as indicated in FIG. 15.

FIG. 20 is a cross section view as indicated in FIG. 15.

Figure 21:
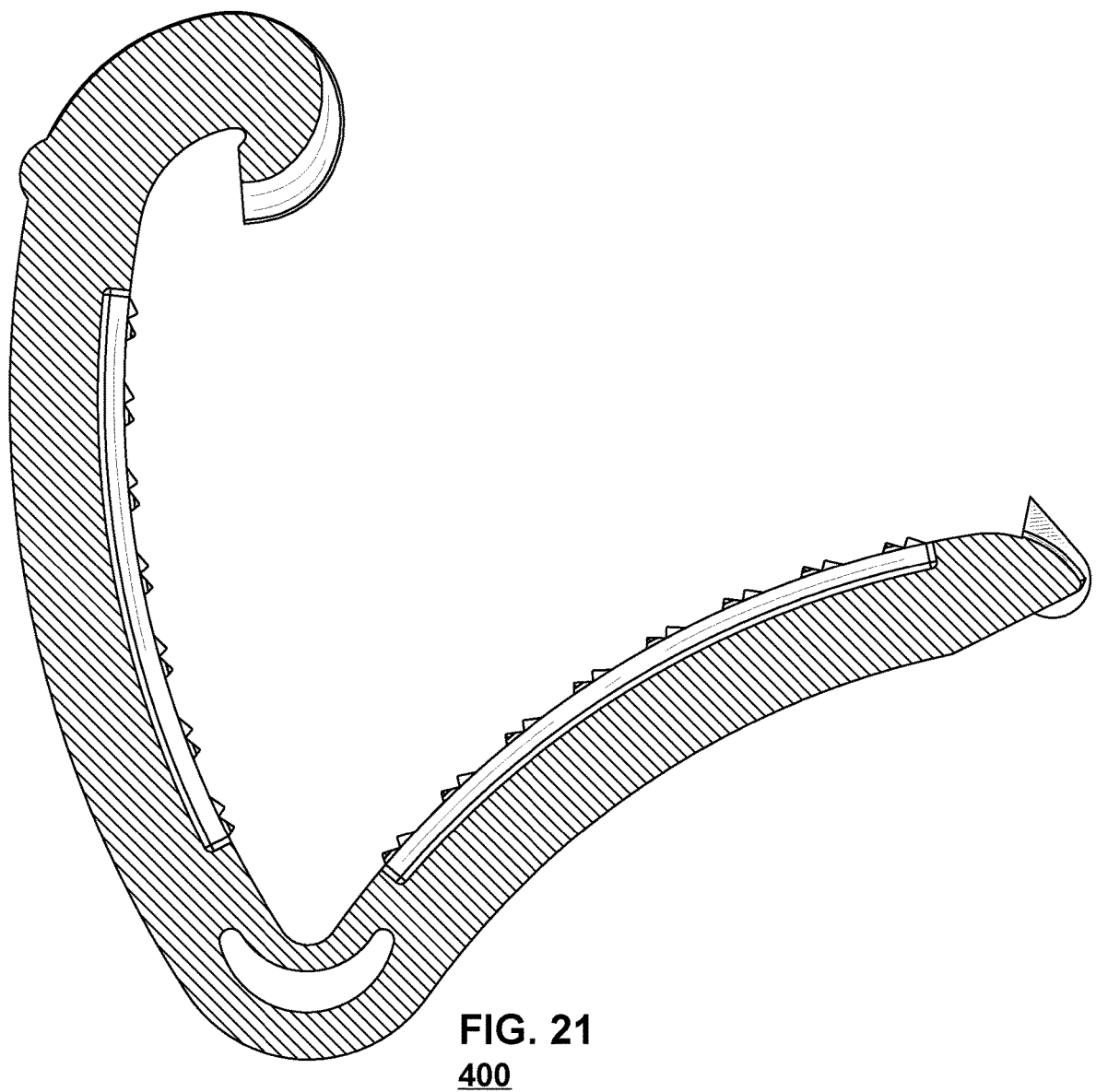
FIG. 21 is a left side elevation of the cross section indicated in FIG. 19.

FIG. 21 is a left side elevation of the cross section indicated in FIG. 19.

Figure 22:
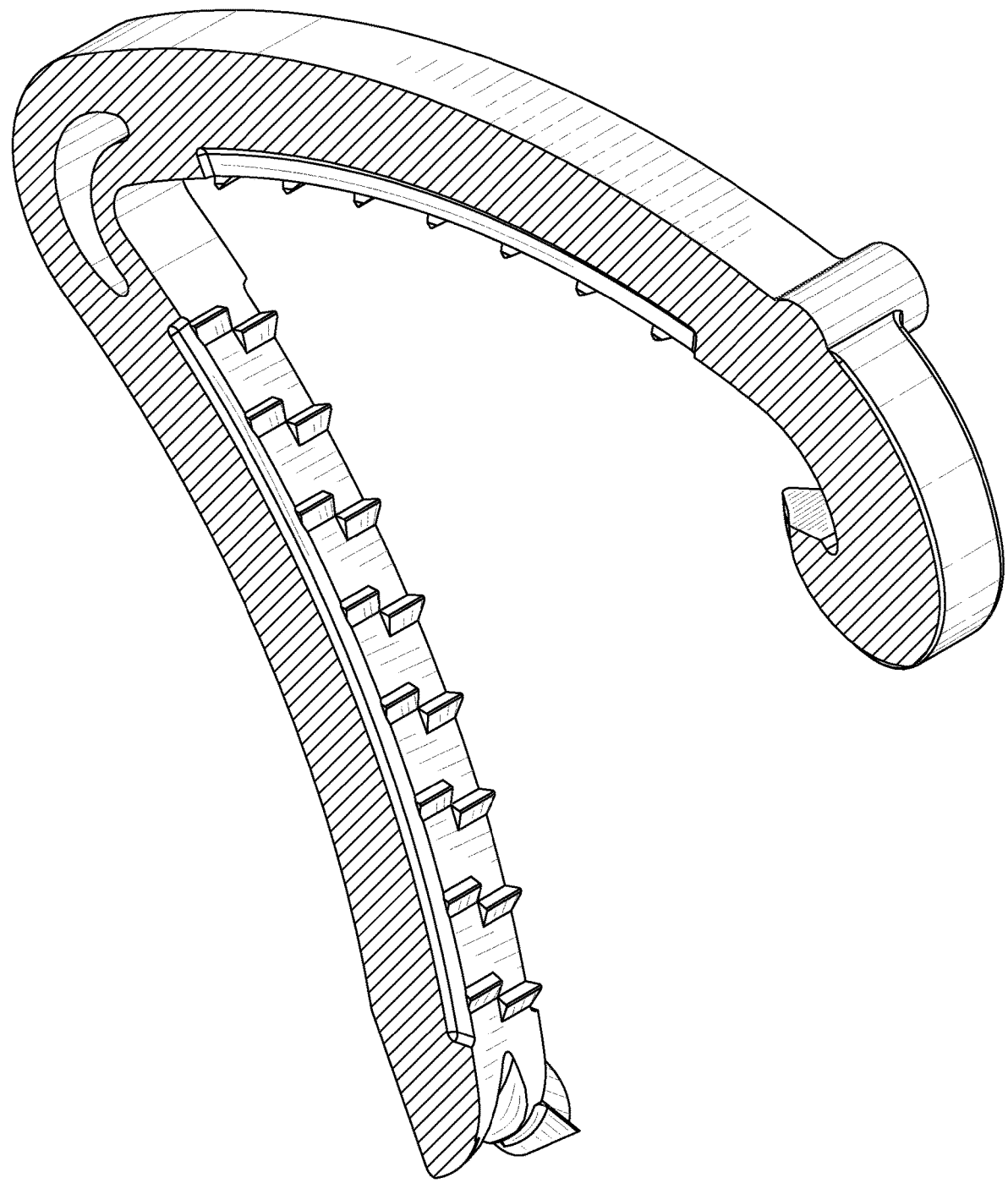
FIG. 22 shows the cross section of FIG. 21 using a top, front, left, perspective view of ligation clip 400 without other element numbers obscuring the image.

FIG. 22 shows the cross section of FIG. 21 using a top, front, left, perspective view of ligation clip 400 without other element numbers obscuring the image.

Figure 23:
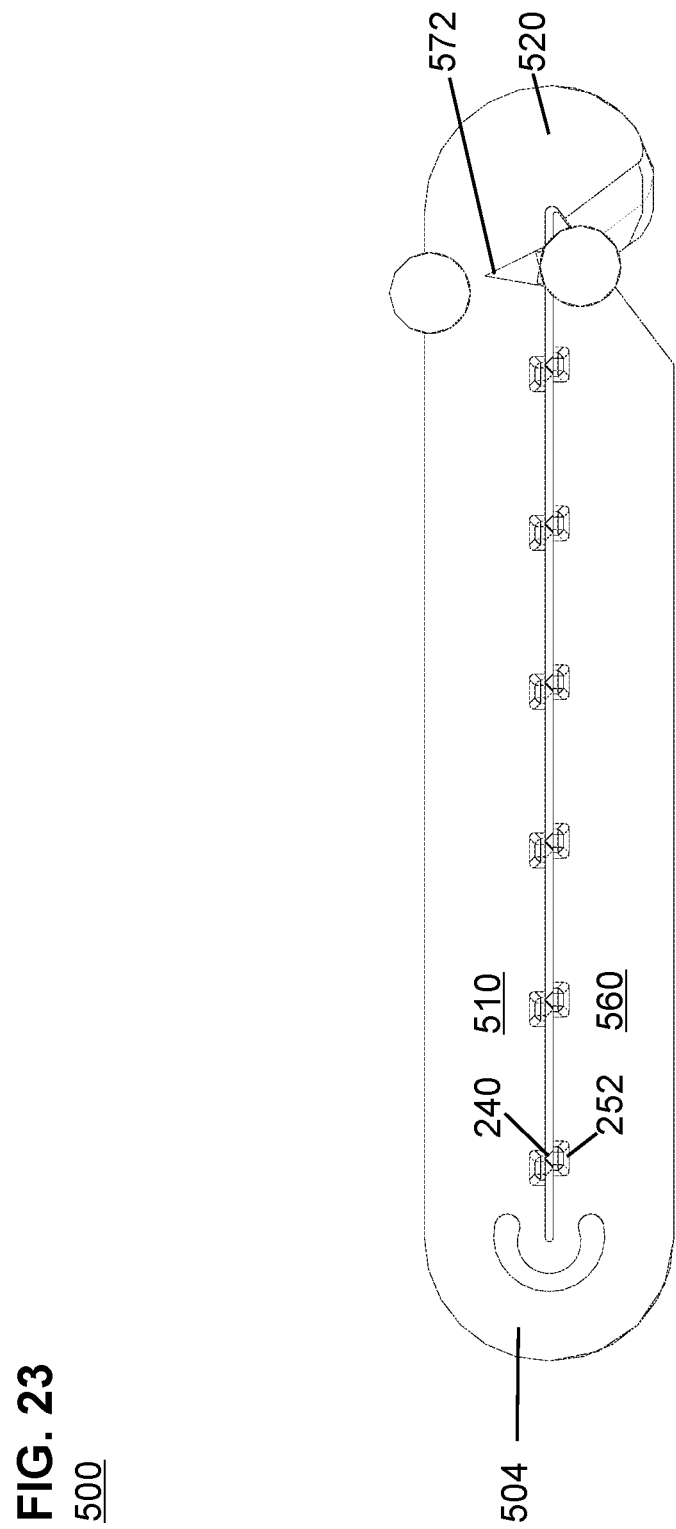
FIG. 23 shows ligation clip 500 in a left elevation view of a cross section that removes clutter from the gripper teeth on the right side of the ligation clip 500.

FIG. 23 shows ligation clip 500 in a left elevation view of a cross section that removes clutter from the gripper teeth on the right side of the ligation clip 500.

A Variety of Tissue Trap Widths.

Those of skill in the art will recognize that if tissue traps 250 can be sized for use with a single tissue plow 240 as with the single tooth tissue traps 252 shown above, or with a pair of tissue plows 240 as shown with double tooth tissue traps 254 shown above, or as merged tissue traps 256 handling seven or eight tissue plows 240 as shown above, then the number of tissue plows 240 per tissue trap 250 is not constrained. Likewise, as shown in connection with ligation clip 200, not all tissue traps 250 need to be the same width within a particular ligation clip. For example, a set of eight tissue plows could be associated with four tissue traps 250 with:

One tissue plow for the first tissue trap;
Two tissue plows for the second tissue trap;
Three tissue plows for the third tissue trap;
Two tissue plows for the fourth tissue trap.

Within a single ligation clip, the pattern of tissue plows and tissue traps does not need to be the same on all leg/side couplets. A second leg/side pair couplet having eight tissue plows may have:

Two tissue plows for the first tissue trap;
Four tissue plows for the second tissue trap; and
Two tissue plows for a third tissue trap.

Alternatives and Variations

Tissue Plow Alignment with Gripper Tooth.

While the examples discussed in this application have shown tissue plows 240 to be aligned with one of the sets of gripper teeth, this is not a requirement to benefit from the teachings of the present invention. One of skill in the art will appreciate that having some or all of the tissue plows be extensions of particular gripper teeth would have some appeal with respect to forming a mold and providing structural support for the tissue plow but a tissue plow operates to help move tissue into the tissue trap to stop the progression of lateral migration of the closed ligation clip. The operation of the tissue plow is independent of the operation of the gripper teeth.

Hook End.

The examples set forth in this disclosure universally show the hook end 120 on the concave leg 110 as that is a common configuration. Nothing in this disclosure limits the placement of the hook end to be on the concave leg 110. One of skill in the art will appreciate that the benefits of the present disclosure could be enjoyed even if the hook end was on the convex leg and the tissue piercing points were moved to the concave leg.

Straight Leg Ligation Clips.

Those skilled in the art will know that ligation clips are commonly in a curved shape as discussed above. However, not all ligation clips are curved. Straight leg ligation clips are known in the art and will benefit from the teachings of the present disclosure with respect to tissue plows and tissue traps working to limit ligation clip migration. FIG. 23 shows ligation clip 500 in a left elevation view of a cross section that removes clutter from the gripper teeth on the right side of the ligation clip 500. Ligation clip 500 has a first leg 510 with a hook end 520 that engages with a second leg 560 with a pair of tissue piercing points (only left side tissue piercing point 572 visible here). The first leg 510 is connected to the second leg 560 via hinge 504.

As with the other ligations clips previously discussed, ligation clip 500 may have the left set of gripper teeth offset from the right set of gripper teeth on first leg 510 and the left set of gripper teeth offset from the right set of gripper teeth on the second leg 560.

Ligation clip 500 uses single tooth tissue traps 252 that are each associated with a single tissue plow 240. Those of skill in the art will appreciate that a straight leg ligation clip could be created using double tooth tissue traps, merged tissue traps, or combinations of various sizes of tissue traps.

Gripper Teeth.

Those of skill in the art will appreciate that while the ligation clips (100, 200, 300, and 400) shown in this disclosure had the left set of gripper teeth 118 offset from the right set of gripper teeth 128 on concave leg 110 and the left set of gripper teeth 268 offset from the right set of gripper teeth 278 on convex leg 160, that this particular arrangement is not required by this disclosure. Other arrangements and interactions are possible. For example, the right set of gripper teeth could be aligned with the left set of gripper teeth for a given leg. Further the gripper teeth for the concave leg 110 could run across the width of the concave leg 110 and the gripper teeth for the convex leg 160 could run across the width of the convex leg 160. As long as the gripper teeth on one leg interact with the gripper teeth on the opposite leg to provide the desired gripping function, the arrangement of the gripper teeth is not limited.

A design for a particular ligating clip might use gripper teeth on only one leg and rely on the interaction of the gripper teeth with a flat side of the opposing leg. Alternatively, the opposing leg could have valleys that are aligned with the gripper teeth so that the captured tissue is forced down into the valleys of the opposing leg. As is evident, the specifics of the gripper teeth patterns are not central to the teachings with respect to the use of tissue traps and tissue plows.

Hinges.

Those of skill in the art will appreciate that the teachings of the present disclosure are not reliant on the particular type of hinge used for the ligating clip. For example, a hinge without a hinge void 106 may be used in some ligating clips. Other more complicated hinges with more than one component may be used and still benefit from the migration resistance afforded by the combination of tissue traps and tissue plows.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A ligation clip comprising: a hinge at a proximal end of the ligation clip connecting a first leg to a second leg; a hook to allow the first leg and the second leg from the ligation clip to become engaged to hold the ligation clip in a closed position with an inner side of the first leg facing an inner side of the second leg; the first leg having a set of gripper teeth that extends outward from the inner side of the first leg; the first leg having an outer side of the first leg opposite the inner side of the first leg; a first face between the proximal end and a distal end of the ligation clip and including the hinge; the first face not including the inner side of the first leg or the outer side of the first leg; a second face between the proximal end and the distal end of the ligation clip and including the hinge, the second face on an opposite side from the first face; and a midline plane located halfway between the first face and the second face; at least one tissue trap near the inner side of the first leg; the tissue trap defining a space within the first face of the ligation clip between the inner side of the first leg and the outer side of the first leg; the at least one tissue trap adapted to receive tissue; at least one tissue plow extending from an edge of the at least one tissue trap outward away from the inner side of the first leg and also away from the midline plane; wherein the ligation clip, after closure upon body tissue, resists movement of the first face in a first direction that is: perpendicular to the first face; and away from the midline plane; and wherein after closure of the ligation clip, the ligation clip resists movement of the first face in the first direction as the set of at least one tissue plow drives tissue into the at least one tissue trap so that trapped tissue resists further movement of the ligation clip in the first direction.

2. The ligation clip of claim 1 wherein the first leg, the second leg, and the hinge are all part of one component and the hinge has a hinge void to accommodate a change from being in an open position to being in the closed position.

3. The ligation clip of claim 1 wherein the ligation clip has a set of bosses for engagement with a ligation clip applier device.

4. The ligation clip of claim 1 wherein the ligation clip has at least one tissue piercing point to pierce through tissue that would impede the closure of the ligation clip.

5. The ligation clip of claim 1 wherein the first face on the first leg has only one tissue trap near the inner side of the first leg between the proximal end and the distal end, and wherein the at least one tissue plow comprises several tissue plows extending from the one tissue trap.

6. The ligation clip of claim 1 wherein the at least one tissue trap comprises at least a first tissue trap and a second tissue trap, and the at least one tissue plow comprises a first number of tissue plows extending from the first tissue trap, wherein the first number is not equal to a second number of tissue plows extending from the second tissue trap.

7. The ligation clip of claim 1 wherein the at least one tissue trap comprises more than one tissue trap, and each tissue trap has an equal number of tissue plows extending therefrom.

8. The ligation clip of claim 1 wherein at least one of the at least one tissue plow extends into a portion of a gripper tooth in the set of gripper teeth on the inner side of the first leg.

9. The ligation clip of claim 1 wherein within the set of gripper teeth, the ligation clip has at least one gripper tooth that is not associated with any of the at least one tissue plow.

10. The ligation clip of claim 1 wherein the first face of the ligation clip has two bosses that extend away from the first face and thus further from the midline plane; each of the at least one tissue plow has a plow tip located at a maximum distance from the midline plane; and none of the plow tips extend beyond a plane containing the first face.

11. The ligation clip of claim 1 wherein the ligation clip in the closed position is not curved.

12. The ligation clip of claim 1 wherein the ligation clip in the closed position is curved.

13. The ligation clip of claim 1 packaged in a cartridge with other ligation clips for loading a clip applier wherein the cartridge, the ligation clip and the other ligation clips are sterilized for use in a sterile field.

* * * * *